United States Patent [19]

Reis et al.

[11] Patent Number: 4,648,262

[45] Date of Patent: Mar. 10, 1987

[54] MICROVISCOSIMETER

[76] Inventors: August K. Reis, Faistenberger Strasse 1, 8000 Muenchen 90; Michael Fiala, Uferweg 15, 8031 Wessling; Jochen R. Heimann, Diplomingenieur, Roentgenstrasse 30, 8012 Ottobrunn, all of Fed. Rep. of Germany

[21] Appl. No.: 881,474

[22] Filed: Jul. 1, 1986

Related U.S. Application Data

[63] Continuation of Ser. No. 709,907, Mar. 7, 1985, abandoned.

[51] Int. Cl.[4] ............................................. G01N 11/12
[52] U.S. Cl. ............................................................ 73/57
[58] Field of Search ............................................. 73/57

[56] References Cited

U.S. PATENT DOCUMENTS

| | | | |
|---|---|---|---|
| 2,259,525 | 10/1941 | Landis | 73/57 |
| 2,414,864 | 1/1947 | Gardner | 73/57 |
| 2,778,220 | 1/1957 | Kuhlmann et al. | 73/57 |
| 3,967,934 | 7/1976 | Seitz et al. | 73/57 |
| 4,276,383 | 6/1981 | Leighton et al. | 73/57 |
| 4,308,750 | 1/1982 | Steinman | 73/57 |
| 4,388,823 | 1/1983 | Garnaud et al. | 73/57 |
| 4,466,275 | 8/1984 | Thone | 73/57 |

OTHER PUBLICATIONS

Belonenko, A Viscometer with Magnetic Lift, Patent Associated Literature, 1-1975.

Irving et al, Viscometer, Dept. of Electronics and Electrical Engineering, The University of Glasgow, 11-1970.

*Primary Examiner*—Stewart J. Levy
*Assistant Examiner*—Hezron E. Williams
*Attorney, Agent, or Firm*—Robert T. Gammons

[57] ABSTRACT

A viscosimeter of the kind wherein a capillary tube containing a fluid, the viscosity of which is to be measured, and a metal ball is supported so that the ball will gravitate from the top of the tube to the bottom and a magnet is used to periodically raise the ball in the capillary and release it. The viscosity is determined by the rate of descent of the ball in the capillary tube.

7 Claims, 15 Drawing Figures

MICROVISCOSIMETER

This is a continuation of co-pending application Ser. No. 709,907 filed on Mar. 7, 1985, now abandoned.

BACKGROUND OF THE INVENTION

Apparatus for measuring the viscosity of liquids are well known, for example, such apparatus is shown and described in German Patent Nos. DT-OS 1015625 and DT-OS 2204878 and also in U.S. Pat. No. 4,388,823. These patents provide for obtaining measurements by elevating a metallic ball in a tube filled with a liquid, the viscosity of which is to be measured by means of a permanent magnet or electromagnet, allowing the ball to fall and measuring the lapse of time that it takes the ball to fall through a predetermined distance. The equipment shown in these patents requires considerable time to set up so that the liquid undergoes change in viscosity with lapse of time or exposure, hence, it is not possible to obtain accurate measurements without the use of anticoagulants or other chemicals. Furthermore, the aforesaid devices are not only inappropriate, but require relatively large quantities of liquid and, in particular, if used for measuring the vicosity of blood, require that the blood sample be taken by means of a syringe, which is highly objectionable to many patients. Obtaining samples of blood by pricking the fingertip and drawing the sample by means of a capillary provides such a small quantity of blood as not to be sufficient for use with the aforesaid equipment.

It is an object of this invention to provide a viscosimeter which can be easily manipulated, prepared for use quickly without substantial lapse of time, thus to minimize any appreciable change in viscosity from the time of taking the sample to the time of measuring the viscosity without the need for adding anticoagulants or other chemicals so that unprepared blood may be measured which enables obtaining accurate and repeatable results, requires no greater volume of blood than can be conveniently obtaining by pricking the fingertip and drawing the sample by means of a capillary which enables selecting the measuring cycle according to the viscosity of the liquid and provides for using expendable, low-cost capillaries. Further objects are to provide a microviscosimeter of the kind wherein a capillary tube is used to take samples of the fluid, the viscosity of which is to be measured, provided with a metal ball arranged to free fall within the tube when the latter is supported at an angle and a holder therefor for supporting the capillary tube at a selected angle for fluids of different viscosity, which can be heated to maintain the capillary tube at a constant temperature during measuring, and which is provided with a window which enables observing the condition of the fluid and the descent of the ball during the measuring operation. Other objects are to provide, in combination with the holder, a preheater for preheating a series of capillary tubes to the temperature of the holder preparatory to taking measurements to thus enable rapid processing of a series of capillaries and to provide two-part capillaries with a precisely fabricated outer part and an inner part less precisely fabricated which when inserted into the outer part takes the configuration of the outer part.

SUMMARY OF THE INVENTION

As herein illustrated, the viscosimeter comprises a holder containing an elongate bore for removably receiving an elongate capillary tube containing a sample of the liquid, the viscosity of which is to be measured, and a ball comprised of magnetic material, means for supporting the holder in a position such that the ball will gravitate from one end of the capillary tube to the other, magnetic means supported for movement along a path relative to the capillary tube to intermittently move the ball from the other end to the one end and, during the interval between movement from the one end to the other end, permitting the ball to be moved by gravity from the one end to the other end, means for measuring the rate of movement of the ball at spaced intervals along the length of the capillary tube as the ball gravitates from the one end to the other end, means for converting the rate of movement to viscosity and means for heating and maintaining the holder and capillary tube at a predetermined temperature during measuring. Desirably, the holder is in the form of a block of metal containing a bore dimensioned to receive the entire length of the capillary tube and bores at opposite sides thereof for receiving thermetic fluid for heating the block and capillary tube to said predetermined temperature or, alternatively, electric heating elements and regulating means for obtaining the same temperature. The means for supporting the holder is adjustable and provides for supporting the holder at different angular positions. The block comprising the holder contains a slot longitudinally of the bore within which the capillary tube is received, defining a window through which the movement of the ball can be observed. There are apertures in the block at opposite sides of the bore within which the capillary is received, spaced longitudinally thereof, within which are contained sensing devices for sensing the movement of the ball and the lapse of time it takes for the ball to move from one sensing means to the other and circuitry for converting the lapse of time into terms of viscosity. The magnetic means is mounted for movement relative to the capillary tube on a rotor rotatable in a direction to move the ball along a path from the lower end of the capillary tube to the upper end thereof and there is a motor for driving the rotor in rotation to repeatedly move the magnetic means from the lower end to the upper end of the capillary tube at intervals such as to raise the ball to the top of the capillary tube and then to allow it to gravitate to the bottom. There is circuitry for controlling rotation of the rotor and, hence, the lapse of time between cycles of operation and means within the circuitry for converting the lapse of time to viscosity and displaying the viscosity. The capillary tube may be comprised of two parts and constructed of relatively inexpensive material so as to be expendable.

The invention will now be described in greater detail with reference to the accompanying drawings, wherein.

Figure 15:
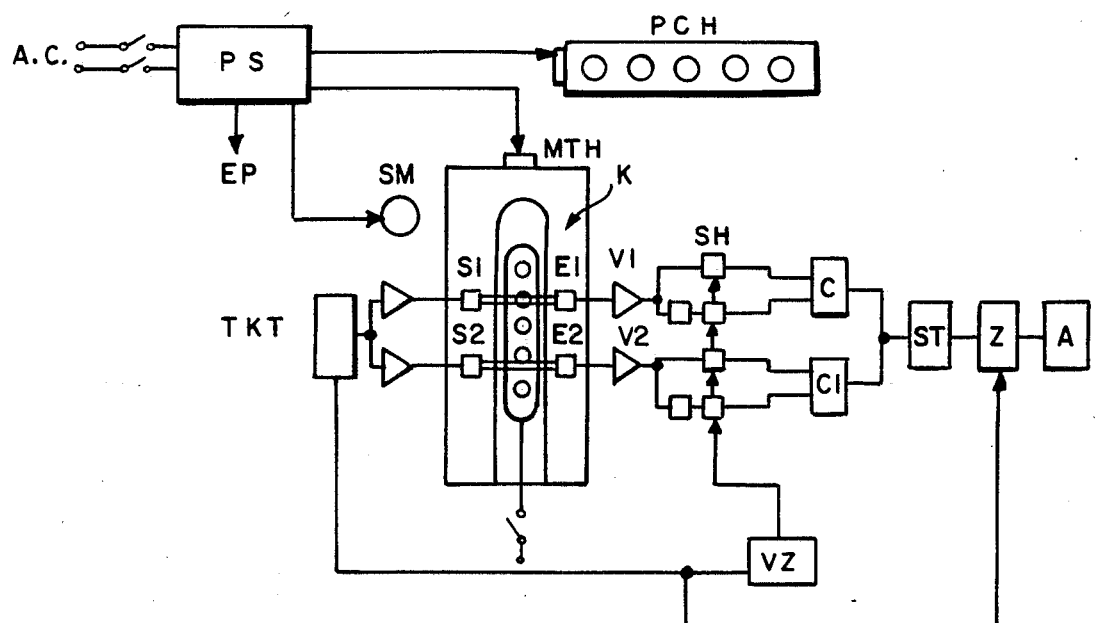

FIG. 15 diagrammatically illustrates the control system circuitry.

Figure 5:
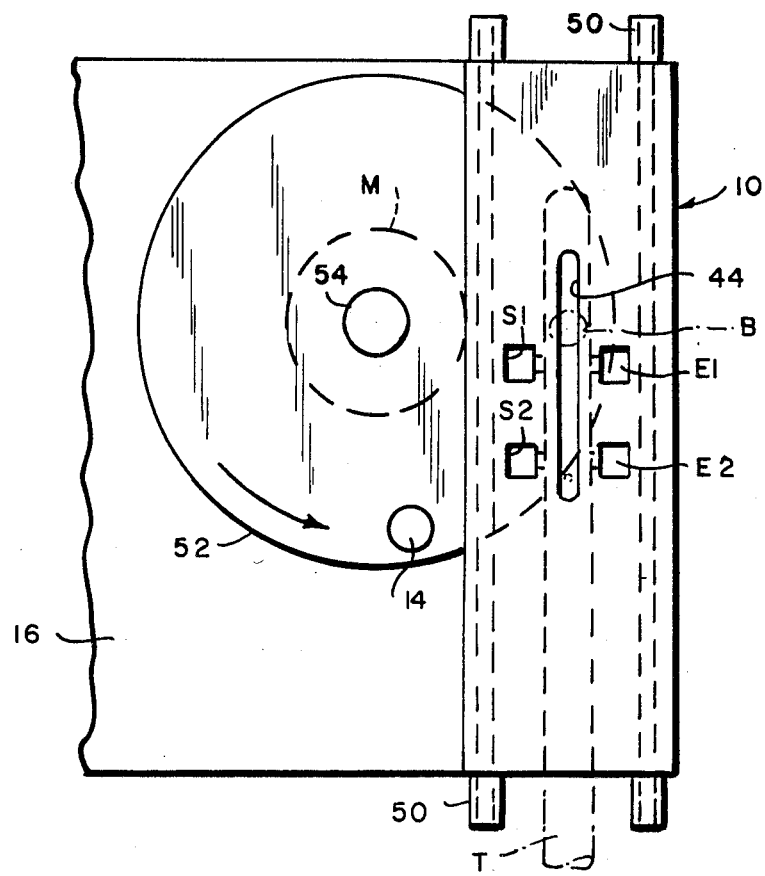
FIG. 5 is a framentary elevation showing supporting structure for supporting the holder for the capillary and a rotatably supported magnet for intermittently raising the ball within the capillary tube.
Figure 6:
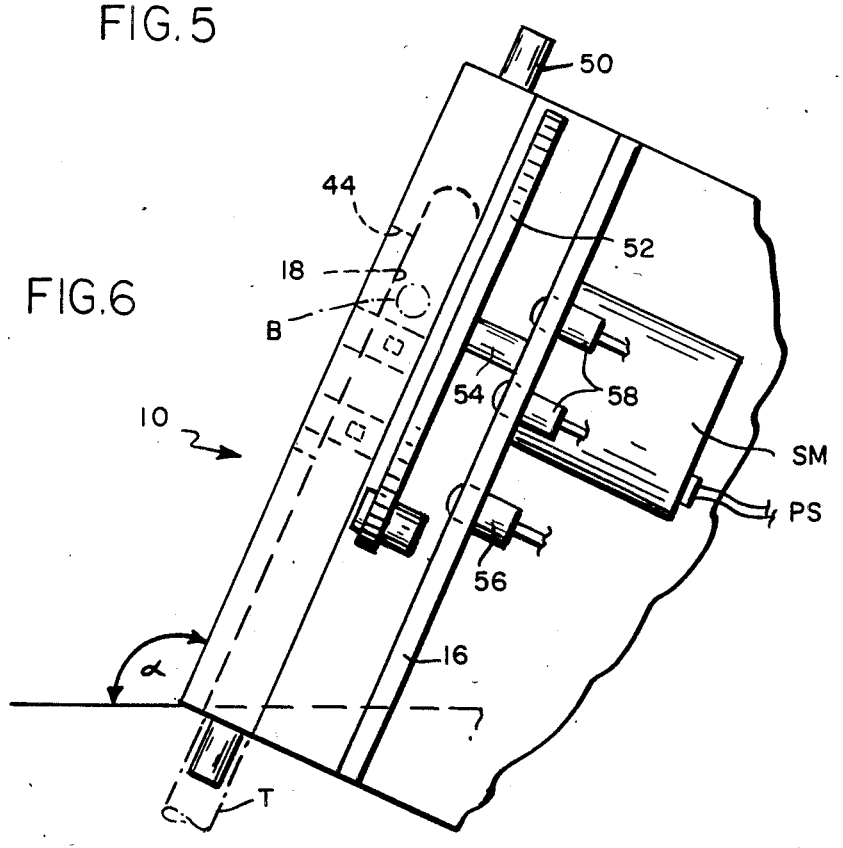
FIG. 6 is an elevation taken on the line 6—6 of FIG. 5.

Referring to the drawings, FIGS. 5 and 6, there is shown a holder 10 for receiving a capillary tube, for receiving a fluid, the viscosity of which is to be measured, a metallic ball B for gravitational movement from an upper end of the capillary tube toward the lower end thereof and a rotatably supported magnet 14 rotatable relative to the holder 10 and the capillary tube supported thereby to raise the ball in the capillary tube and then allow it to gravitate to the lower end. Desirably, the holder 10 for the capillary tube and the rotor for rotating the magnet 24 are supported on a mounting plate 16, the inclination of which can be adjusted to provide for optimum measurement of liquids according to their viscosity, as will appear hereinafter.

Referring to FIGS. 1 to 4, the holder 10 comprises an elongate block of metal, for example, aluminum, of rectangular cross section containing longitudinally thereof a bore 18 open at one end, as shown at 20, and closed at the other end, as shown at 22. The bore 18 is dimensioned longitudinally and diametrically to receive the capillary tube T. The bore 18 is dimensioned to receive a 60 microliter capillary tube.

Figure 1:
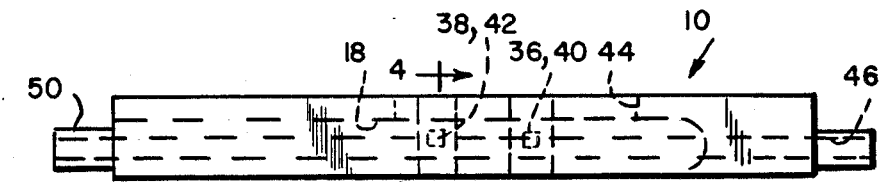
FIG. 1 is a side view of the supporting body for the capillary tube.
Figure 2:
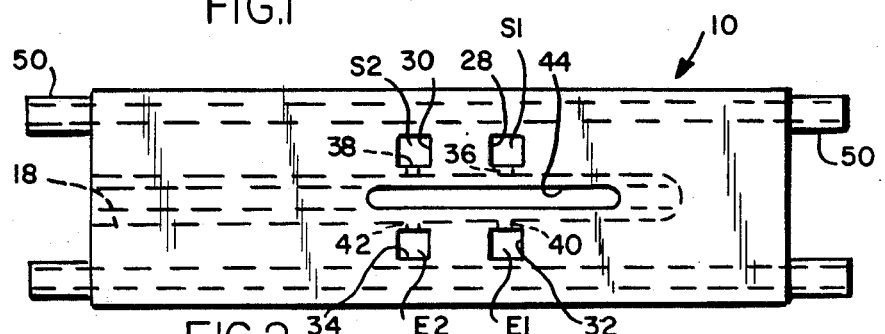
FIG. 2 is a plan view as seen from the top side of FIG. 1.
Figure 3:
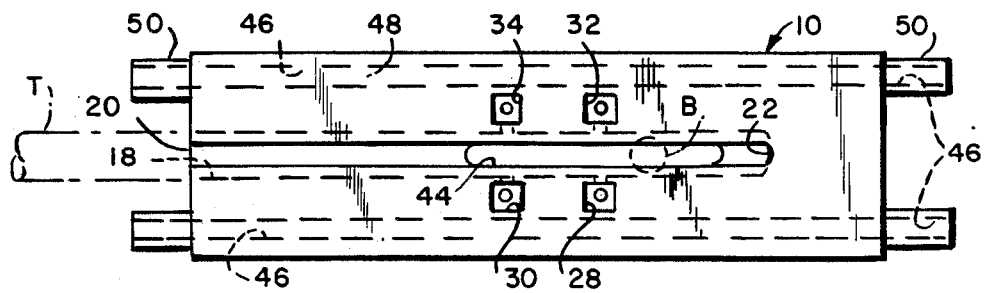
FIG. 3 is a plan view as seen from the bottom side of FIG. 1.
Figure 4:
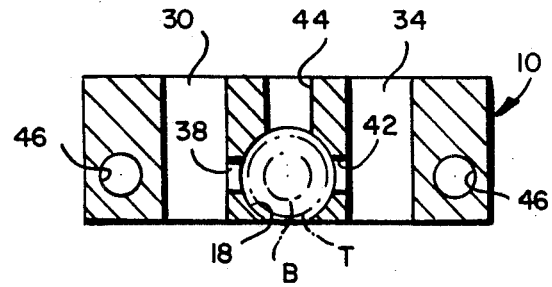
FIG. 4 is a section taken on the line 4—4 of FIG. 1.

At opposite sides of the bore 18, there are longitudinally-spaced openings 28 and 30 on one side and 32 and 34 at the other side. The openings 28, 30, 32 and 34 extend through the holder from one side to the other, as shown in FIG. 4, and are connected by apertures 36, 38, 40 and 42 to the bore 18. The apertures 36 and 40 are positioned diametrically opposite each other and the apertures 38 and 42 are positioned diametrically opposite each other. Sensing means of suitable kind, for example, an electro-optic transmitter S1,S2 is placed in each of the openings 28 and 30 and a receiver E1,E2 is placed in each of the openings 32 and 34 so that movement of the ball in the capillary tube, as will be described hereinafter, will interrupt the beams passing from the transmitter S1,S2 to the receivers E1,E2. The interruption of the beams, as will be related hereinafter, will produce a pulse in circuitry designed to translate the interruption into terms of viscosity. Desirably, a window slot 44 is provided in the holder 10 in the upper side, as shown in FIGS. 2 and 4, into the bore 18 so that movement of the ball in the capillary tube may be observed.

To insure bubble-free measurement, the window provided by the slot 44 is illuminated by means of a lamp 56, FIG. 6, positioned on the support 16 behind the holder 10 to enable observing whether there are air bubbles in the capillary tube and/or whether the capillary tube is dirty, which would lead to errors in the measured results. For different liquids, it is possible to select a preferred spectral range by choice of special lamps 58 also shown positioned on the plate 16 behind the holder 10.

Two additional bores 46—46 are provided at opposite sides of the bore 18 which extend from end to end of the holder. These bores provide for receiving thermetic fluid by means of which the holder is heated to a predetermined optimum temperature for the fluid being processed. Nipples 50—50 are threaded into the opposite ends of the bores 46—46 for receiving the thermetic fluid, the temperature of which can be controlled. Optionally, electric heating elements may be placed in the bore 46—46 connected to suitable electrical circuitry and provided with temperature control means.

As related heretofore, the holder 10 which supports the capillary tube T is supported at an inclined angle, as shown in FIG. 6, so that the ball B within the capillary tube, when raised to the upper end of the tube and released, will gravitate to the bottom, passing in its course downwardly the sensing elements, to wit, the transmitters S1,S2 and receivers E1,E2. The magnet 14 which may be a permanent magnet or electromagnet is supported on a rotatable disk 52, FIGS. 5 and 6, adjacent the holder 10 at the rear side. As shown in FIG. 6, the disk 52 is mounted to a shaft 54 supported with its axis at right angles to the supporting plate 16 and to the holder 10. A motor SM fixed to the rear side of the supporting plate 16 drives the shaft 54 and thus rotates the disk 52. The axis of the shaft 54 is supported relative to the holder 10 so that as the disk rotates in counter-clockwise direction, as shown in FIG. 5, the magnet 14 moves along a circular path about a center which intersects the bore 20 so that the magnet travels upwardly along the length of the bore and of the capillary tube positioned within the bore through an arc of approximately 60 degrees.

The circuitry for controlling operation of the apparatus is illustrated in a block diagram in FIG. 15 and comprises a pulse generator TKT, electro-optic transmitters S1 and S2, receivers E1 and E2, amplifiers V1 and V2, sample and hold circuitry SH, comparators C and C1, a control ST, delaying circuitry VZ, a counter Z and a digital display A. In the circuitry, the capillary tube is indicated at K. The pulse generator TKT controls the transmitters S1 and S2 in such a way that the falling ball in the capillary is monitored by the receivers E1,E2. The amplifier V transmits signals to sample and hold circuits SH and comparators C. Depending upon the time which the falling ball requires for passing between S1/E1 and S2/E2, the counter Z is initiated. The result is displayed on display unit A. The delaying circuit VZ serves for the purpose of registering the maximum signals with the receivers E1,E2. A power supply PS is provided for heating the holder, a preheater PCH for preheating the capillaries, driving the motor SM And supplying power to the circuitry.

Figure 8:
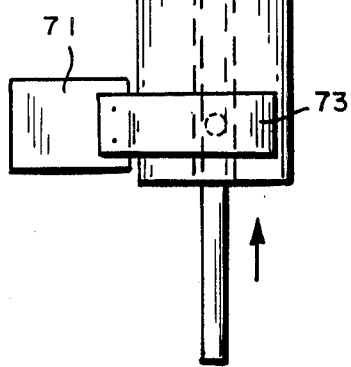
FIG. 8 is a section taken transversely of FIG. 7.
Figure 12:
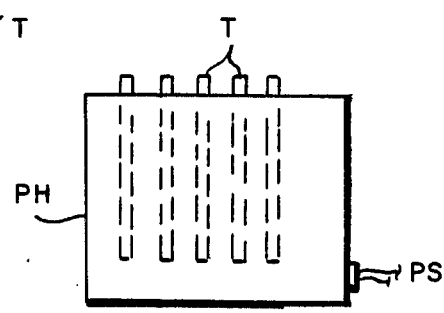
FIG. 12 is an elevation of a preheater for preheating a plurality of capillary tubes to the temperature of the holder by means of which meansurements are taken.

The preheater PGH, FIGS. 8 and 15, for preheating the capillary tubes prior to taking measurements is in the form of a block containing holes for receiving a plurality of capillaries.

In use, the holder 10 is heated to the desired temperature, whereupon a preheated capillary tube T equipped with a ball B is removed from the preheater PH, approximately 100 microliters of blood are drawn from the fingertip or other part of the body by capillary, and the capillary containing the blood sample is then inserted into the bore 18 for measuring at a predetermined temperature consistent with the viscosity of the liquid being tested for viscosity. For blood, the heat capacity of the capillary device that is, its capacity for holding heat should be 50 to 1 in relation to the sample. Measurement of viscosity is started by starting the motor SM and thereafter proceeds automatically until the motor circuitry is deactivated. Activation of the circuitry drives the motor SM which, in turn, rotates the disk 52 so that each time that the magnet 14 is relative to from the lower end of the capilary tube to the upper end thereof through the aforesaid angle, the ball is raised within the capillary tube from the lower end to the upper end. As the magnetic ball 14 moves beyond the upper end of the capillary tube, its magnetic influence on the ball ceases and the ball gravitates toward the lower end of the capillary tube. Its progress can be seen through the slot 44. As the ball gravitates, it first blocks the light from the transmitter S1 to the receiver E1 and thereafter blocks the light from the transmitter S2 to the receiver E2. The lapse of time between blocking the light from the upper sensing devices to the lower sensing devices is measured by the circuitry shown in FIG. 15 and translated into terms of viscosity and displayed by the digital display A. The disk 52 will continue to rotate so long as the circuitry is energized so that the ball is repeatedly elevated in the capillary tube and allowed to fall so that 4 to 8 measurements may be made before sufficient change takes place in the liquid as, for example, coagulation, which would make the measurement inaccurate.

Figure 13:
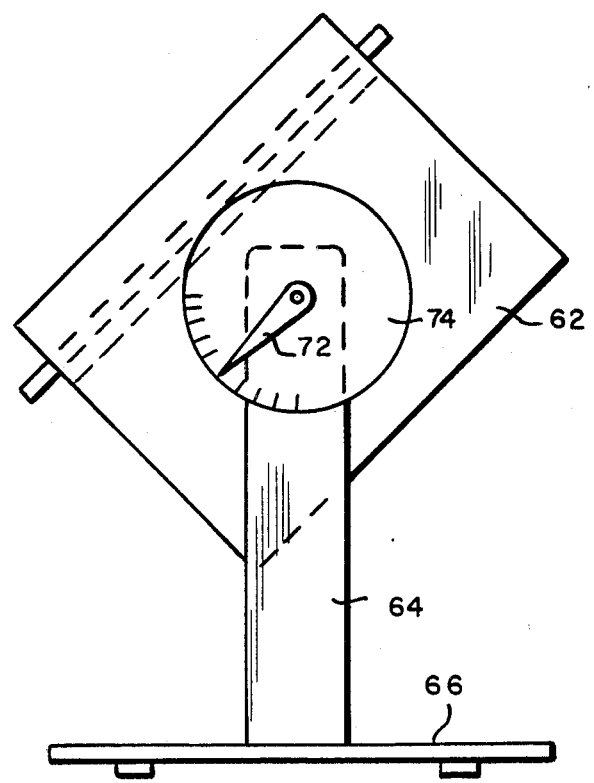
FIG. 13 is a side elevation of a support for supporting the viscosimeter at an inclination.
Figure 14:
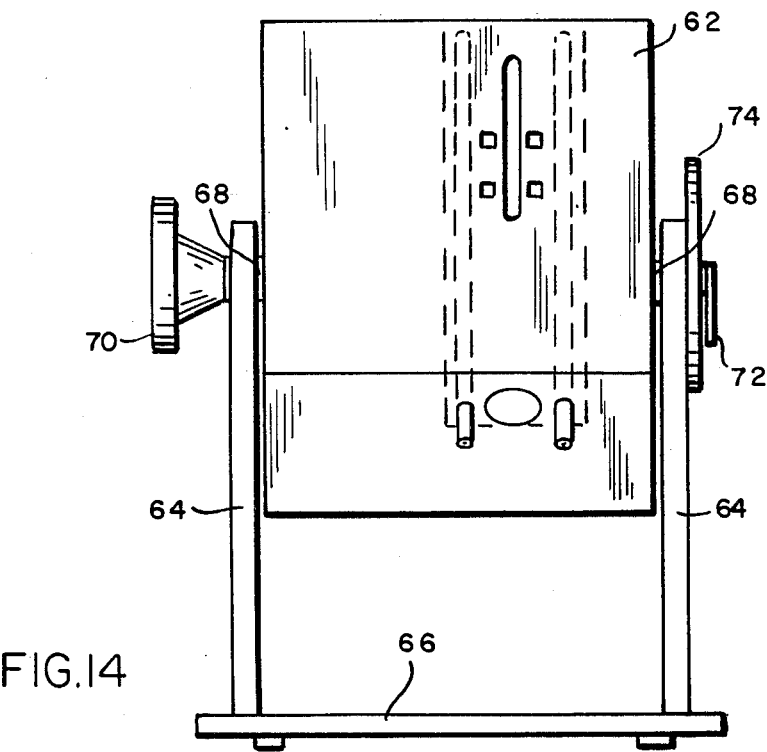
FIG. 14 is a front elevation of FIG. 13.

Optimum results for particular liquids can be achieved by adjusting the inclination of the holder 10. For this purpose, there is shown in FIGS. 13 and 14 a support structure 62 mounted between the upper ends of vertically-disposed, spaced, parallel legs 64—64 fixed at their lower ends to a base plate 66. The support structure is pivotally mounted between the legs by means of bolts 68—68 journaled in the upper ends of the legs. One bolt has a knob 70 threaded thereon to provide for fixing the support at a selected angle of inclination. (The other bolt has fixed to it a pointer 72 movable relative to a plate 74 bearing indicia representing angles of inclination.)

In order to avoid measurement during lifting of the ball within the capillary tube, it is advisable to provide a control device so that measurement is only made when the ball passes the sensors in the correct direction.

Figure 7:
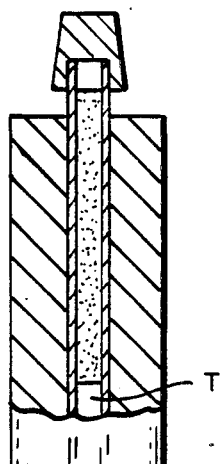
FIG. 7 is an elevation of a typical capillary tube disposed in a holder with a magnet for holding the ball.
Figure 9:
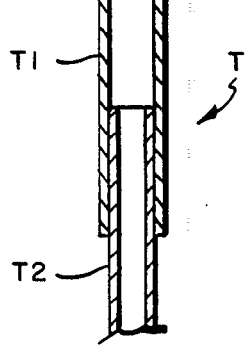
FIG. 9 is a fragmentary elevation of a two-part capillary tube.
Figure 10:
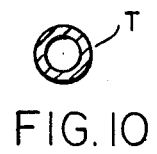
FIG. 10 is a cross section of a capillary tube of circular cross section.
Figure 11:
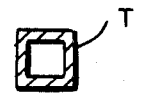
FIG. 11 is a cross section of a capillary tube of rectangular cross section.

The capillary tubes T, FIG. 7, are desirably disposable, and have the advantage that only a very small quantity of liquid is necessary to obtain accurate measurement. Such tubes are readily available already sterilized and should include, for ease of handling, the metal balls B. The balls can be held during filling at a predetermined position by a permanent magnet 70 which is, in turn, held to the measuring tube by a spring clip 73. Desirably, the capillary tube is comprised of two parts, FIG. 9. Since the measurement with the light-sensitive means necessitated comparatively high accuracy, the two part capillary can be constructed with an outer part T1 which is exactly fabricated and an inner part T2 less exactly fabricated which, when inserted thereinto, takes the exact configuration of the accurately formed outer part. The capillary may be of circular or rectangular cross section, FIGS. 10 and 11, and may be comprised of any suitable plastic or artificial material. As herein illustrated, the holder 10 is desirably comprised of aluminum and the bore 18 is dimensioned to receive a 60 microliter capillary tube such as are readily available for all kinds of usages. The disk 52 may be comprised of any suitable material, for example, plexiglas.

It should be understood that the present disclosure is for the purpose of illustration only and includes all modifications or improvements which fall within the scope of the appended claims.

What is claimed is:

1. Apparatus for automatically measuring the viscosity of liquids comprising a holder, a support for the holder, means pivotally mounting the holder on the support for angular movement about a horizontal axis, said means including a knob for effecting angular adjustment of the holder to dispose the holder at a selected angle of inclination and means movable by such angular movement to indicate the angle of inclination, said holder containing a bore of predetermined longitudinal and diametrical dimensions, said bore being open at the lower end and closed at the upper end, a capillary tube disposed in said opening containing the liquid, the viscosity of which is to be measured, said capillary tube containing a steel ball, said holder containing at diametrically-opposite sides of said bore between the upper and lower ends of the bore at diametrically-opposite sides of the bore, longitudinally-spaced first openings in communication with the bore, sensing means positioned in said first openings, said holder containing at diametrically-opposite sides of said bore at right angles to said longitudinally-spaced first openings, opposed second openings, one of which is of a length extending along the axis of the bore at least the distance between said first spaced openings, a source of light mounted to the holder adjacent the other of said second openings such as to illuminate the capillary tube to enable observation of the tube through said elongate opening in the one side, a disk mounted to the support for rotation about a horizontal axis at right angles to the axis of rotation of the holder, a permanent magnet mounted to the periphery of the disk, movable by rotation of the disk in a circular path in a plane parallel to the holder such as to alternatively lift the ball from the lower end of the capillary tube to the upper end thereof to release the same so that it gravitates to the lower end, sensing means operable to determine the internal of time that the ball takes to gravitate from the upper to the lower one of said openings according to the selected angle of inclination and said holder containing at diametrically-opposite sides of the bore, parallel bores by means of which the holder can be heated to a predetermined temperature and maintained at said temperature throughout the measuring of the viscosity.

2. Apparatus according to claim 1 wherein the heating means comprises electrical heating elements and means for regulating the temperature of the heating elements.

3. Apparatus according to claim 1 wherein control circuitry is provided for determining the desired measuring cycle.

4. Apparatus according to claim 1 wherein the capillary tube is constructed in two parts.

5. Apparatus according to claim 1 wherein the cross section of the the capillary tube is circular.

6. Apparatus according to claim 1 wherein the cross section of the capillary tube is rectangular.

7. Apparatus according to claim 1 wherein the heat capacity of the capillary tube is at least 20 to 1 and, preferably, 50 to 1 or more in relation to the heat capacity of the fluid sample.

* * * * *